United States Patent
Heyman

[11] Patent Number: 5,810,834
[45] Date of Patent: Sep. 22, 1998

[54] TIP FORMATION FOR INSERTING A FLEXIBLE MEMBRANE INTO AN EYE

[75] Inventor: Thomas M. Heyman, Chino Hills, Calif.

[73] Assignee: Chiron Vision Corporation, Claremont, Calif.

[21] Appl. No.: 729,768

[22] Filed: Oct. 7, 1996

[51] Int. Cl.[6] .................................................. A61F 9/00
[52] U.S. Cl. ............................................................ 606/107
[58] Field of Search .................. 606/107, 167, 606/161, 166; 128/754

[56] References Cited

U.S. PATENT DOCUMENTS

| | | | |
|---|---|---|---|
| 4,573,998 | 3/1986 | Mazzocco | 623/6 |
| 4,681,102 | 7/1987 | Bartell | 606/107 |
| 4,702,244 | 10/1987 | Mazzocco | 623/6 |
| 4,715,373 | 12/1987 | Mazzocco et al. | 606/107 |
| 4,765,329 | 8/1988 | Cumming et al. | 606/107 |
| 4,834,094 | 5/1989 | Patton et al. | 606/107 |
| 4,836,201 | 6/1989 | Patton et al. | 606/107 |
| 4,919,130 | 4/1990 | Stoy et al. | 606/107 |
| 4,926,877 | 5/1990 | Bookwalter | 128/754 |
| 4,934,363 | 6/1990 | Smith et al. | 606/107 |
| 5,123,905 | 6/1992 | Kelman | 606/107 |
| 5,190,552 | 3/1993 | Kelman | 606/107 |
| 5,275,604 | 1/1994 | Rheinish et al. | 606/107 |
| 5,304,182 | 4/1994 | Rheinish et al. | 606/107 |
| 5,425,734 | 6/1995 | Blake | 606/107 |
| 5,474,562 | 12/1995 | Orchowski et al. | 606/107 |
| 5,494,484 | 2/1996 | Feingold | 606/107 |
| 5,496,328 | 3/1996 | Nakajima et al. | 606/107 |
| 5,499,987 | 3/1996 | Feingold | 606/107 |

*Primary Examiner*—Robert A. Hafer
*Assistant Examiner*—Justine R. Yu
*Attorney, Agent, or Firm*—Banner & Witcoff, Ltd.

[57] ABSTRACT

A tip formation for an instrument for inserting a flexible membrane into an eye is formed at the distal end of a cannula. The cannula has a lumen which directs the flexible membrane through an incision and into the eye. The distal end is beveled so as to provide ease of entry into the incision and to orient the discharge opening for the flexible membrane at an inclination to the longitudinal axis of the lumen. The cannula walls about the beveled end are tapered to form a smaller sized end without impeding the advance of the membrane.

20 Claims, 4 Drawing Sheets

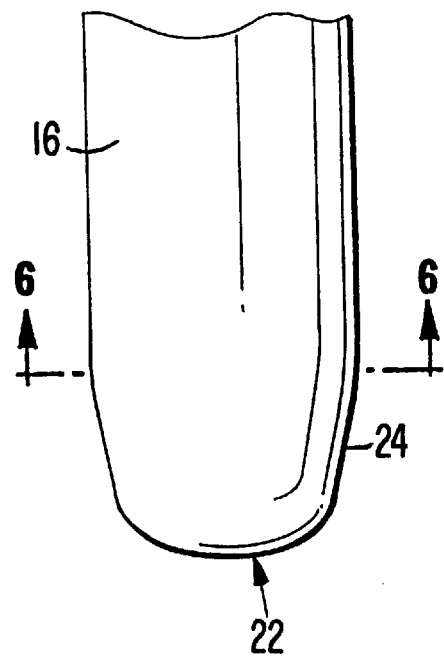
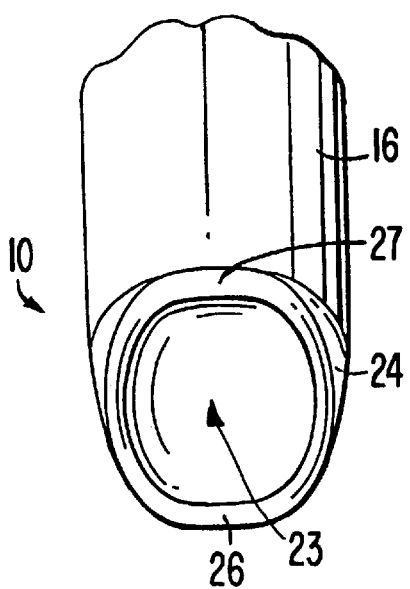
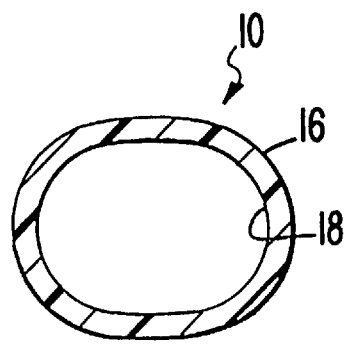

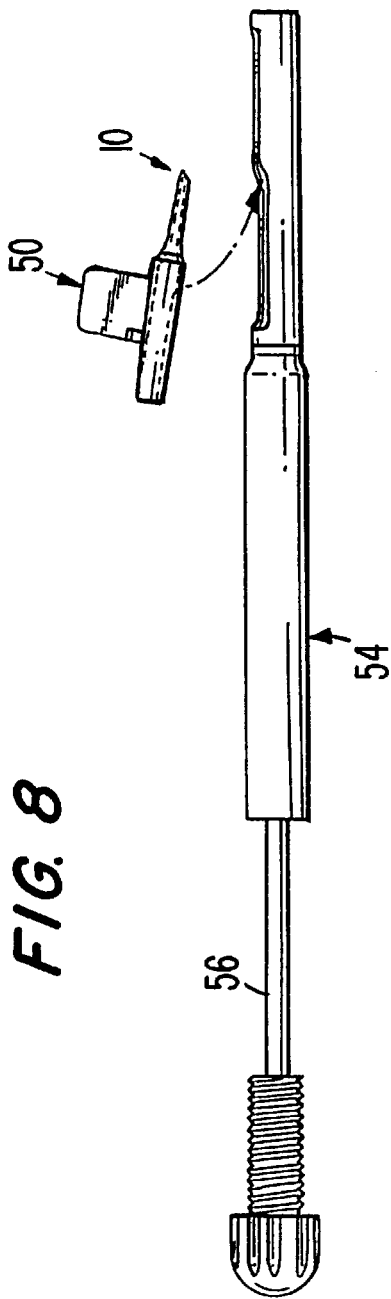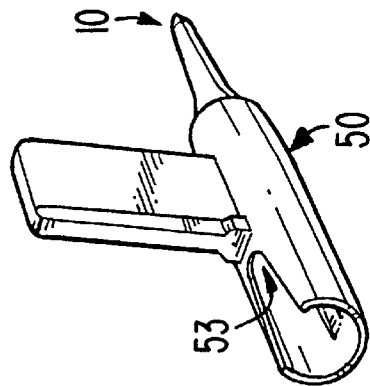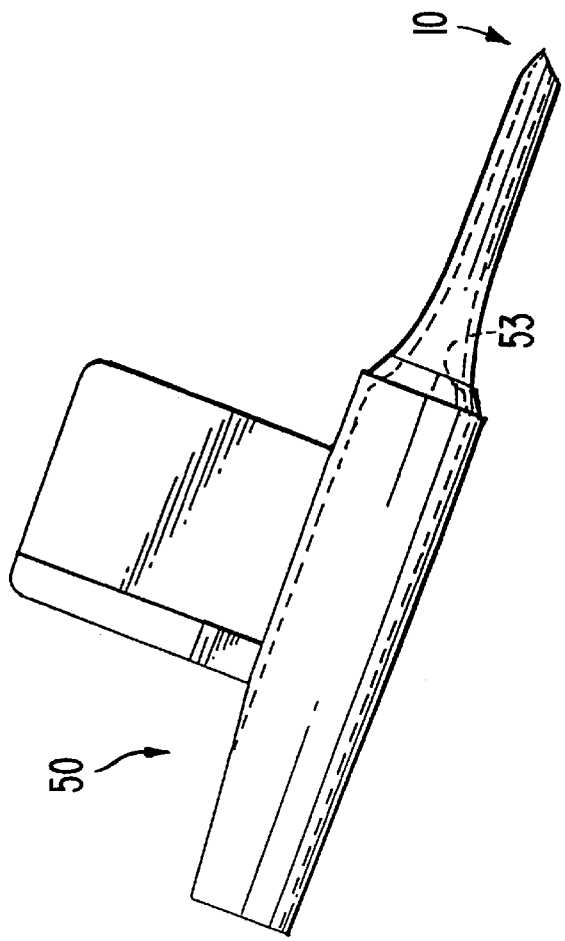

TIP FORMATION FOR INSERTING A FLEXIBLE MEMBRANE INTO AN EYE

FIELD OF THE INVENTION

The present invention pertains to a tip formation for an instrument for inserting a flexible intraocular lens or other flexible membrane into an eye.

BACKGROUND OF THE INVENTION

The natural crystalline lens of the eye plays a primary role in focusing light onto the retina for proper vision. However, vision through the natural lens may become impaired because of injury, or due to the formation of a cataract caused by aging or disease. To restore vision, the natural lens is typically replaced with an artificial lens. An artificial lens may also be implanted as a replacement or a supplement to the natural lens in order to make a refractive or other vision correction.

A natural lens is generally removed through the use of a slender implement which is inserted through a small incision in the eye. The implement includes a cutting tool that is ultrasonically vibrated to emulsify the lens. The emulsified fragments of the lens are aspirated out of the eye through a passage provided in the cutting tool. The slender nature of the implement enables extraction of the lens through a small incision in the eye. The use of a small incision over other procedures requiring a large incision can lessen the trauma and complications experienced during surgery and postoperatively.

The artificial lens is composed of a flexible material so that the lens can be folded and/or compressed to a smaller cross-sectional size, and thus avoid enlargement of the incision during implantation of the lens. To this end, inserters ordinarily include a lens reducing structure which functions to reduce the cross-sectional size of the lens, and a cannula with a lumen to direct the lens into the eye. The lens reducing structure has taken many different forms including, for example, hinged sections which close about a lens and tapering lumens which compress the lens as it is advanced toward the eye. The cannula is a slender, thin-walled tube at its distal end that guides the lens through the incision and into the eye. The lumen along the distal portion of the cannula generally has a substantially uniform configuration and size (i.e., with only a slight taper for molding purposes) to avoid additional high forces needed to further compress the lens. By maintaining a substantially uniform lumen, the risk of rupturing the thin walls is alleviated.

While there is great interest in making the distal end of the inserter as narrow as possible, there are practical considerations which have limited the extent to which the size of the cannula can be reduced. For instance, as mentioned above, large inwardly directed forces are needed to further reduce a lens which is already tightly compressed. As a result, merely reducing the diameter of the lumen at its distal end to achieve a smaller cannula will at some point increase the inwardly directed forces so as to impede the advance of the lens or cause rupture of the walls. Also, further thinning of the walls to reduce the cannula without narrowing the lumen will also at some point lead to rupture of the cannula walls during use.

SUMMARY OF THE INVENTION

The present invention pertains to a tip formation for an instrument used to insert a flexible intraocular lens or other flexible membrane into an eye. The present tip formation is formed at the distal end of a cannula which directs a lens into the eye. The distal end is beveled so as to provide ease of entry into the incision and to orient the discharge opening for the lens at an inclination to the longitudinal axis of the lumen. The cannula walls about the beveled end are tapered to form a smaller sized end without impeding the advance of the lens. The tip formation reduces the circumference and diameter of the cannula distal end without a concomitant reduction of the cross-sectional area of the path through which the lens is passed or a lessening of the thickness of the cannula's sidewalls. As a result, use of an inserter with the present tip formation enables the size of the incision to be minimized and the ease of inserting the instrument into the eye enhanced.

BRIEF DESCRIPTION OF THE DRAWINGS

FIG. 4 is a partial, top plan view of the tip member.

FIG. 5 is a partial, bottom view of the tip member taken along line 5—5 in FIG. 2.

FIG. 6 is a cross-sectional view taken along line 6—6 in FIG. 4.

FIG. 8 is an exploded, side elevational view of a second embodiment of an inserter with a tip formation in accordance with the present invention.

FIG. 9 is a side elevational view of the cartridge of the inserter of the second embodiment.

FIG. 10 is a perspective view of the cartridge.

DETAILED DESCRIPTION OF THE PREFERRED EMBODIMENTS

The present invention pertains to a tip formation for an instrument used to insert a flexible intraocular lens or other flexible membrane into an eye. The tip formation is formed on the distal end of a cannula and could be used with virtually any lens insertion device which uses a tubular member to direct the lens into an eye.

Figure 2:
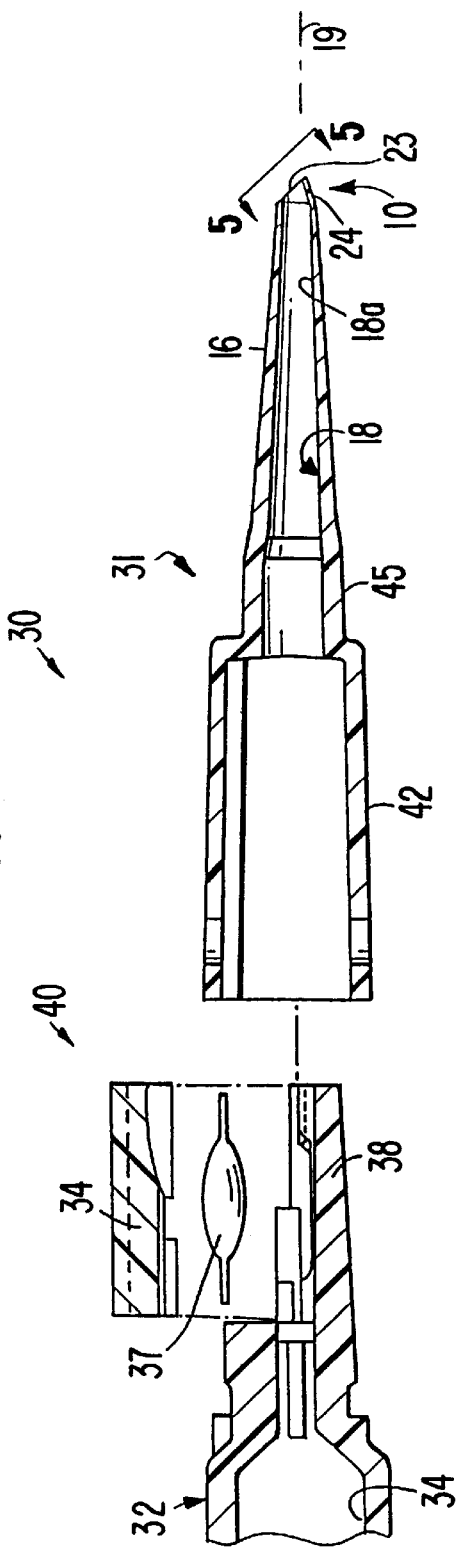
FIG. 2 is an exploded cross-sectional view taken along line 2—2 in FIG. 1.
Figure 3:
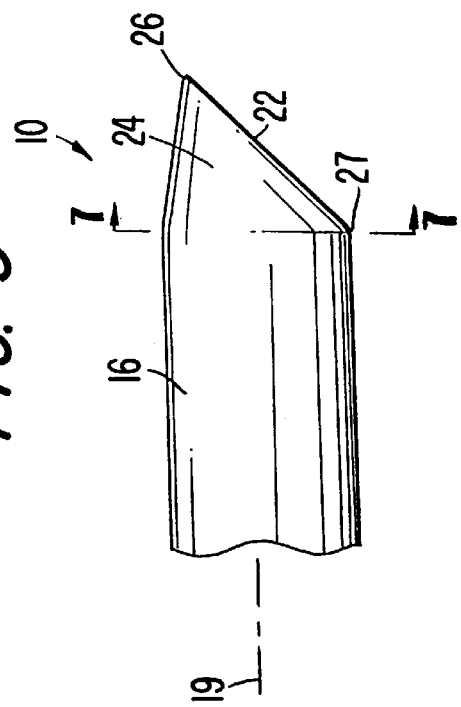
FIG. 3 is a partial, side elevational view of the tip member of the inserter showing the present tip formation.
Figure 7:
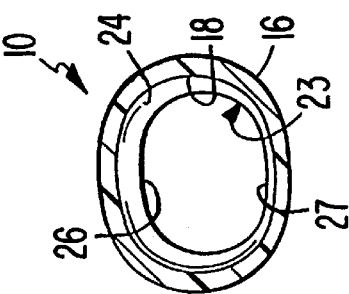
FIG. 7 is a cross-sectional view taken along line 7—7 in FIG. 3.

In a preferred embodiment, tip formation 10 of the present invention is formed on the distal or free end 22 of a cannula 16 (FIGS. 2–7). The cannula includes a lumen 18 which defines a generally linear path along a longitudinal axis 19 for directing a lens of reduced size through a small incision in an eye (FIGS. 2 and 3). The distal end of lumen 18 is open to form a discharge opening 23 for implanting the lens into an eye. The distal end 22 of cannula 16 is beveled to orient the discharge opening 23 at an inclination to longitudinal axis 19. The term beveled as used in this application is intended to indicate a surface which is oriented at least in part at an inclination to the longitudinal axis of the lumen, irrespective of the angle of the inclination, whether the cut is linear or curved, or whether the surface is regular or irregular.

The beveled free end 22 defines a front edge 26 and a rear edge 27 of discharge opening 23 (FIGS. 2, 3, 5 and 7). The wall portion 24 of cannula 16 that extends between rear edge 27 and front edge 26 converges in a forward direction. In the preferred construction, the tapering of wall portion 24 begins at an imaginary perpendicular plane extending through rear edge 27 and continues to front edge 26. Further, wall portion 24 preferably conforms substantially to the shape of a cone segment, such that the entire periphery converges toward longitudinal axis 19. Nonetheless, the convergence of wall portion 24 could have a different shape, be discontinuous, or extend along only a part of the distance between rear edge 27 and front edge 26. The convergence of wall portion 24 toward axis 19 functions to reduce the size of the cannula's distal end to ease insertion of the inserter instrument into the incision, and to minimize the size of the incision. Moreover, the reduction of the distal end 22 is achieved without thinning of the cannula walls or impeding the advance of the lens into the eye.

The provision of a beveled free end across a tubular member creates a discharge opening which is larger than the discharge opening would be if formed to be perpendicular to the passage of the tubular member. In accordance with the present invention, the additional space gained by providing an inclined discharge opening is advantageously used to reduce the size of the free end of the cannula. In other words, wall portion 24 adjacent the inclined discharge opening 23 converges to narrow the external surface of cannula 16 forward of rear edge 27 without causing the discharge opening to have a smaller area than the perpendicular cross-sectional area of lumen 18 at rear edge 27.

In the preferred construction, the distal walls of the cannula are formed as a thin tube to minimize the size of the tip to be passed into the eye. The portion 18a of lumen 18 which is rearward or upstream of rear edge 27 has a substantially uniform inner configuration and size (i.e., with the conventional slight taper for molding purposes) in order to direct the lens into the eye without the application of additional high forces associated with further compression of a lens. The discharge opening 23 is inclined at a 45° angle to axis 19 to define front edge 26 and a rear edge 27 (FIGS. 2 and 3). Wall portion 24 converges forwardly at an included angle of about 20° (i.e., 10° relative to axis 19) from an orthogonal plane aligned with rearward edge 27. Despite the reduced exterior of the cannula, the perpendicular cross-sectional area of lumen 18 at rearward edge 27 is substantially equal to the area of discharge opening 23 to avoid impeding the advance of the lens into the eye (FIGS. 5 and 6). In a preferred example, the area of the discharge opening 23 and the perpendicular cross-section of the lumen at rearward edge 27 are equal to about 0.004 square inches.

Many variations can be made to the preferred tip formation without departing from the spirit of the invention. For example, the converging wall portion 24 can converge at a changing rate or begin converging at locations forward or downstream of rear edge 27. Also, the beveled surface can be set at different inclinations or provided with a non-linear shape. The area of the discharge opening may also, of course, continue to be somewhat larger than the perpendicular cross-sectional area at the rear edge 27, if the convergence begins forward of the rear edge or a smaller level of convergence is used.

Figure 1:
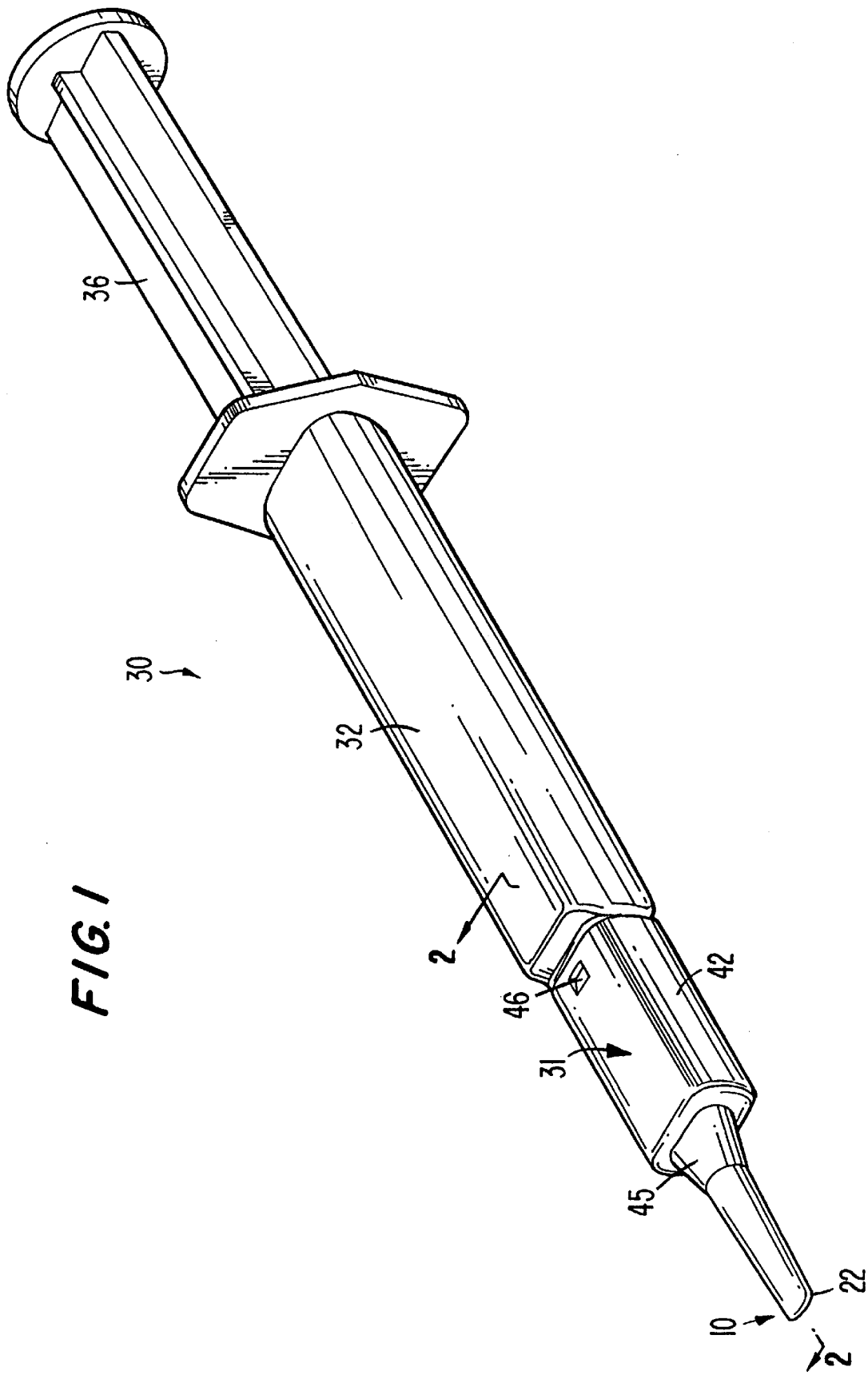
FIG. 1 is a perspective view of an inserter with a tip formation in accordance with the present invention.

In the preferred embodiment, tip formation 10 is an integral part of a discrete, one-piece tip member 31 for an inserter 30 (FIGS. 1 and 2). Inserter 30 has a construction as disclosed in U.S. patent application Ser. No. 08/286,557, filed Aug. 5, 1994, which is hereby incorporated by reference. In general, inserter 30 includes a tubular member 32, a cover 34, and a plunger 36 along with tip member 31. Tubular member 32 has a rearwardly opening cavity 34 for receiving plunger 36, and a forwardly projecting shelf 38 for receiving a lens 37. Cover 34 overlies the shelf to enclose the lens and define station 40 for holding and folding the lens.

In use, the lens is placed onto shelf 38 and enclosed with cover 34. Base portion 42 of tip member 31 is pushed over the shelf and cover, and locked in place with a latch 46 to form an integral unit with tubular member 32. plunger 36 is pushed forward to advance the lens through station 40, which folds the lens, and into tapering segment 45 of lumen 18. The combined folding and compression effects of station 40 and tapering segment 45 define a lens reducing structure which reduces the size of lens to a cross-sectional size small enough to fit through the narrow incision in the eye. Portion 18a of lumen 18 has a substantially uniform configuration and size to guide the lens up to the rear edge 27 of discharge opening 23 without any further significant compression of the lens. The lens is then fed through tip formation 10, out discharge opening 23, and into the eye. Yet, despite the convergence of wall portion 24, the area of the discharge opening is still the same or larger than the perpendicular cross-sectional area of the lumen at the rear edge 27.

Alternatively, tip formation 10 could be formed on the end of other inserters which use a cannula to direct the lens into an eye, irrespective of the type of lens reducing structure which is used, whether the inserter is composed of one piece or multiple pieces, or whether the tip formation is a part of a cartridge or inserter tip. For example, tip formation 10 could be provided on the distal end a cartridge 50 (FIGS. 8–10). Cartridge 50 has a tapering lumen 53 within the cartridge as a lens reducing structure. After the lens is loaded into the lumen, the cartridge is placed into insertion device 54 having a plunger 56 for moving the lens into an eye.

Similarly, tip formation 10 can also be formed on the end of a cartridge as disclosed in U.S. Pat. No. 5,494,484 to Feingold, which is hereby incorporated by reference. In this case, the cartridge includes hinged sections as the lens reducing structure which close about the lens to reduce the cross-sectional size of the lens. The cartridge is then placed within an insertion device which advances the lens into an eye.

As another example, tip formation 10 could be used with an inserter which has a one-piece tubular member as disclosed in U.S. patent application Ser. No. 08/721,349 filed Sep. 26, 1996, now pending, by Cicenas et al., which is hereby incorporated by reference. In this device, the lens reducing structure includes a laterally movable compressor for providing an initial reduction in the lens' cross-sectional size, and a tapering lumen which further reduces the size of the lens as it is moved toward the eye. Tip formation 10 is formed at the distal end of the cannula in the same way as described above.

The above discussion concerns the preferred embodiments of the present invention. Various other embodiments as well as many changes and alterations may be made without departing from the spirit and broader aspects of the invention as defined in the claims.

I claim:

1. A tip formation for an instrument for inserting a flexible membrane into an eye, said tip formation comprising a cannula having a lumen for directing the flexible membrane into an eye, a beveled free end including a front edge and a rear edge, and an opening in said beveled free end for discharging the flexible membrane from said lumen, said cannula having a first generally uniform portion immediately rearward of said rear edge and a second portion between said front and rear edges converging toward said front edge at a greater rate than said first portion.

2. A tip formation in accordance with claim 1 in which said discharge opening has an area which is substantially equal to or greater than a perpendicular cross-sectional area of said lumen in said first portion at said rear edge of said discharge opening.

3. A tip formation in accordance with claim 1 in which said first portion of said cannula extends along a longitudinal axis of said cannula, and said beveled free end is inclined at an angle of about 45 degrees relative to the longitudinal axis.

4. A tip formation in accordance with claim 1 in which said first portion of said cannula includes opposing wall portions which are substantially parallel to one another.

5. A tip formation in accordance with claim 1 in which said second portion of said cannula converges the entire distance between said rear edge and said front edge.

6. A tip formation in accordance with claim 1 in which said second portion of said cannula substantially conforms to a cone segment.

7. A tip formation in accordance with claim 1 in which said first portion of said cannula includes opposing wall portions that converge toward said rear edge.

8. A tip formation for an instrument for inserting a flexible membrane into an eye, said tip formation comprising a cannula having a lumen for directing a flexible membrane into an eye, a beveled free end defining a discharge opening for said lumen, said discharge opening including a rear edge and a front edge, a first wall portion immediately rearward of said rear edge, and a second wall portion between said front edge and said rear edge, said second wall portion being inclined relative to said first wall portion, and said discharge opening having an area which is larger than or substantially equal to a perpendicular cross-sectional area of said lumen in said first wall portion at said rear edge of said discharge opening.

9. A tip formation in accordance with claim 8 in which said second wall portion of said cannula converges the entire distance between said rear edge and said front edge.

10. A tip formation in accordance with claim 8 in which said first portion of said cannula includes opposing wall portions that converge toward said rear edge.

11. An instrument for inserting a flexible membrane into an eye, said instrument comprising:

a reducing structure for reducing a cross-sectional size of the flexible membrane; and a tip formation including a cannula having a lumen for directing the flexible membrane into an eye, a beveled free end including a front edge and a rear edge, and an opening in said free end for discharging the flexible membrane from said lumen, said cannula having a first generally uniform portion immediately rearward of said rear edge, and a second portion between said front edge and said rear edge converging toward said front edge at a greater rate than said first portion.

12. An instrument in accordance with claim 11 in which said discharge opening has an area which is substantially equal to or greater than said perpendicular cross-sectional area of said lumen in said first portion at said rear edge of said discharge opening.

13. An instrument in accordance with claim 11 in which said first portion of said cannula extends along a longitudinal axis, and said beveled free end is inclined at an angle of about 45 degrees relative to the longitudinal axis.

14. An instrument in accordance with claim 11 in which said first portion of said cannula includes opposing wall portions which are substantially parallel to one another.

15. An instrument in accordance with claim 11 in which second portion of said cannula converges along the entire distance between said rear edge and said front edges.

16. An instrument in accordance with claim 11 in which said second portion of said cannula substantially conforms to a cone segment.

17. An instrument in accordance with claim 11 which further includes a plunger for advancing the flexible membrane through said lumen and into the eye.

18. An instrument in accordance with claim 11 which further includes an insertion device and a cartridge removably received in said insertion device, wherein said cartridge includes said reducing structure.

19. An instrument in accordance with claim 18 wherein said tip formation is formed as a part of said cartridge.

20. An instrument in accordance with claim 11 in which said first portion of said cannula includes opposing wall portions that converge toward said rear edge.

* * * * *